United States Patent [19]
Yamamoto et al.

[11] Patent Number: 4,965,194
[45] Date of Patent: Oct. 23, 1990

[54] PYRUVATE OXIDASE AND AN ANALYTICAL METHOD USING THE SAME

[75] Inventors: Kazumi Yamamoto; Toshiro Kikuchi; Shigenori Emi, all of Tsuruga, Japan

[73] Assignee: Toyo Boseki Kabushiki Kaisha, Osaka, Japan

[21] Appl. No.: 87,086

[22] Filed: Aug. 19, 1987

[30] Foreign Application Priority Data

Aug. 21, 1986 [JP] Japan ................. 61-196230
Sep. 10, 1986 [JP] Japan ................. 61-213666

[51] Int. Cl.$^5$ ............................. C12Q 1/26
[52] U.S. Cl. ...................... 435/25; 435/189; 435/192; 435/810
[58] Field of Search ............... 435/25, 189, 192, 810

[56] References Cited

U.S. PATENT DOCUMENTS 4,246,342 1/1981 Misaki et al. ................ 435/25

OTHER PUBLICATIONS

Journal of Bacteriology, Oct. 1984, pp. 273–278, vol. 160, No. 1.
"Methods in Enzymology", vol. I, Academic Press Inc., New York, 1955, pp. 482–487.

Primary Examiner—Esther L. Kepplinger
Assistant Examiner—Laurie A. Scheiner
Attorney, Agent, or Firm—Irell & Manella

[57] ABSTRACT

A pyruvate oxidase with excellent thermal stability, which is stable at pH 7.0 for 10 minutes at a temperature of up to 45° C., an analytical method using said pyruvate oxidase, and an analytical reagent used for said method.

12 Claims, 3 Drawing Sheets

PYRUVATE OXIDASE AND AN ANALYTICAL METHOD USING THE SAME

BACKGROUND OF THE INVENTION

1. Field of the Invention

This invention relates to a preparation of pyruvate oxidase with excellent thermal stability, to an analytical method that makes use of this preparation, and to analytical reagents for use in this analysis.

2. Description of the Prior Art

Pyruvate oxidase is classified as EC 1.2.3.3. It is an enzyme that catalyses a reaction that produces acetyl phosphate, carbon dioxide, and hydrogen peroxide from pyruvic acid, inorganic phosphate, and oxygen. Pyruvate oxidase can be used to measure the amount of pyruvic acid in, for example, blood or urine samples, or to measure the enzyme activities of glutamic-pyruvic transaminase, glutamic-oxaloacetic transaminase, lactate dehydrogenase, pyruvate kinase, L-amino-acid oxidase, etc.

It is known that pyruvate oxidase is produced by a variety of microorganisms. For example, it is known to be produced by *Lactobacillus delbrueckii* (B. Maruo, N. Tamiya, compilers, *Enzyme Handbook* (in Japanese), Asakura Bookstore, publisher), *Lactobacillus plantarum* (*J. Bacteriol.*, 160, 273-278 (1984)), microorganisms of the genus Pediococcus, Streptococcus, and Aerococcus (all of the above disclosed in Laid Open Patent Publication No. 58-40465), microorganisms of the genus Leuconostoc (disclosed in Laid Open Patent Publication No. 59-159777), etc. However, the pyruvate oxidase produced by all of these microorganisms has poor resistance to heat (to less than 40° C.). Thus, problems with thermal stability can arise during, for example, the measurements mentioned above of pyruvic acid or other enzymes.

SUMMARY OF THE INVENTION

The preparation of pyruvate oxidase of this invention, which overcomes the above-discussed and numerous other disadvantages and deficiencies of the prior art, has excellent thermal stability, being stable at pH 7.0 for 10 minutes at a temperature of up to 45° C.

In a preferred embodiment, the pyruvate oxidase has the following characteristics:

(1) It catalyzes a reaction that produces acetyl phosphate, carbon dioxide, and hydrogen peroxide from pyruvic acid, inorganic phosphate, and oxygen.
(2) It acts specifically on pyruvic acid.
(3) Its optimum pH is in the vicinity of pH 5.7.
(4) It requires thiamine pyrophosphate and FAD as cofactors.
(5) Its molecular weight is about 160,000 (measured by gel filtration on Sephacryl S-300).
(6) The $K_m$ for pyruvic acid is about $4 \times 10^{-4}$ M.
(7) Its isoelectric point is about 4.4 (measured by electrofocusing with carrier ampholytes).

In a preferred embodiment, the pyruvate oxidase mentioned above is produced by a strain of bacteria of the genus Lactobacillus that has pyruvate oxidase activity.

In a preferred embodiment, the pyruvate oxidase mentioned above is produced by the strain of Lactobacillus sp. TE-6103.

The analytical method of this invention is done with the use of the above-mentioned pyruvate oxidase.

The analytical reagent of this invention contains the above-mentioned pyruvate oxidase, FAD, thiamine pyrophosphate, phosphate, and at least one metal ion selected from magnesium ion, cobalt ion, manganese ion, and calcium ion.

Thus, the invention disclosed herein makes possible the objects of (1) providing a pyruvate oxidase with excellent thermal stability; (2) providing an analytical method by which accurate measurements can be made of pyruvic acid and of other kinds of enzymes and substrates, etc., involved in the enzyme reactions for the production of pyruvic acid, with the use of the said pyruvate oxidase with excellent thermal stability; and (3) providing analytical reagents for use in said analysis that have excellent heat-resistance and that also are stable in solution.

BRIEF DESCRIPTION OF THE DRAWINGS

This invention may be better understood and its numerous objects and advantages will become apparent to those skilled in the art by reference to the accompanying drawings as follows.

DESCRIPTION OF THE PREFERRED EMBODIMENTS

Figure 1:
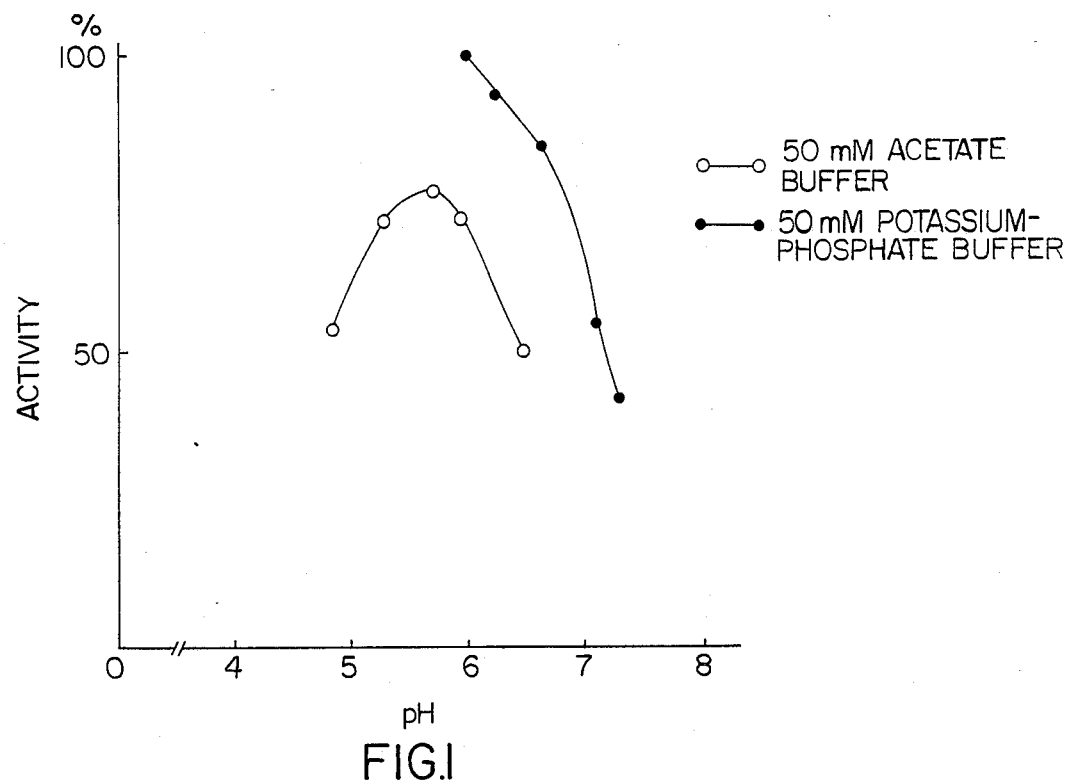
FIG. 1 shows the changes in the activity of the pyruvate oxidase with excellent thermal stability of this invention with changes in the pH.

The inventors of this invention were able to find a pyruvate oxidase with thermal stability that is superior to that of the conventional preparations of pyruvate oxidase. This pyruvic oxidase is produced by a microorganism belonging to the genus Lactobacillus, which was obtained from soil collected in Tsuruga City, Fukui Prefecture, Japan.

The bacteriological characteristics of this microorganism are as follows:

(a) Morphology:
(1) Cell morphology and diameter of rods:
Rods $(0.5-0.7) \times (5-6)$ μm
(2) Gram staining: Positive (3) Acid-fast: Negative
(4) Mobility: Negative
(5) Spores: Negative
(b) Growth on different media:
  (1) Meat broth agar culture:
     Small round colonies were formed within 48 hours at 30° C. Their surfaces were smooth but not shiny. They were pale yellow, and a soluble pigment was not formed.
  (2) Meat broth agar slant culture:
     Growth was poor.
  (3) Meat broth liquid culture:
     Growth occurred by culture at 30° C. for 24 hours and the liquid became turbid.
  (4) Meat broth gelatin stab culture:
     Growth occurred along the line of the stab. The gelatin was not liquified.
  (5) Litmus milk: No change.
(c) Physiological characteristics:
  (1) Reduction of nitrate: Negative
  (2) Denitrification reaction: Negative
  (3) Indole production: Negative
  (4) Hydrogen sulfide production: Negative
  (5) Starch hydrolysis: Negative
  (6) Production of pigments: Negative
  (7) Utilization of citric acid: Negative
  (8) Urease: Negative
  (9) Catalase: Negative
  (10) Oxidase: Negative
  (11) Growth limits: Growth temperature 20°–45° C.
  (12) Oxygen requirements: Facultative anaerobic
  (13) O-F test: Fermentation
  (14) Acid production from sugars
     L-Arabinose: −
     D-Xylose: −
     D-Glucose: +
     D-Mannose: +
     D-Fructose: +
     D-Galactose: −
     Maltose: +
     Sucrose: +
     Lactose: −
     Trehalose: −
     D-Sorbitol: −
     D-Mannitol: +
     Inositol: −
     Rhamnose: −
     Melibiose: +
  (15) Other characteristics:
     β-Galactosidase: Negative
     Arginine dihydrase: Negative
     Lysine decarboxylase: Negative
     Ornithine decarboxylase: Negative
     Tryptophan deaminase: Negative The experimental methods used to identify the bacteriological characteristics reported above were mainly based on the methods given in *Classification and identification of microorganisms* (in Japanese), T. Hasegawa, ed., Gakkai Shuppan Center (1975).

On the basis of the above mentioned bacteriological characteristics, such as that this strain is a gram-positive bacillus, that it is negative for catalase and oxidase, that it produces acid fermentatively from glucose, without producing gas from glucose, etc., we identified this strain with reference to *Bergey's Manual of Determinative Bacteriology*, 8th edition (1974) to be a species of Lactobacillus. Although this strain was very similar to *Lactobacillus delbrueckii*, this strain is different from that species in that this strain produces acid from D-mannitol or melibiose. Therefore, this strain belongs to a species that has been unknown until now, and we named it Lactobacillus sp. TE6103. This strain has been deposited at the Fermentation Research Institute, Agency of Industrial Science and Technology, as FERM BP-1419.

Preferably, the pyruvate oxidase of this invention is produced by the Lactobacillus sp. TE6103 mentioned above, but this invention includes all other pyruvate oxidases with excellent thermal stability produced by other microorganisms belonging to other species or strains of Lactobacillus.

The enzyme of this invention (pyruvate oxidase) with excellent thermal stability is produced by culture of a strain that produces pyruvate oxidase with excellent thermal stability (for example, the Lactobacillus sp. TE6103 mentioned above) by ordinary methods.

As the components of the culture medium to be used, it is possible to use synthetic culture medium or artificial culture medium, provided that they contain a suitable amount of the necessary nutrients, such as a carbon source, a nitrogen source, inorganic substances, and other nutrients, which can be utilized by the strain of microorganism of interest. For example, glucose, sucrose, dextrin, pyruvic acid, molasses, etc., can be used as the carbon source. As the nitrogen source, it is possible to use either inorganic or organic nitrogen compounds, examples of which include natural products containing nitrogen such as peptone, meat extract, yeast extract, casein hydrolysates, etc.; inorganic salts such as ammonium chloride, ammonium sulfate, ammonium phosphate, ammonium nitrate, etc.; organic salts such as ammonium citrate, etc.; amino acids such as glutamic acid, etc.

The microorganism mentioned above can be cultured by the use of the culture medium mentioned above in the ordinary way by a shaking culture or by a aerated culture. The culture temperature is set to be in the range of 20° to 40° C., and preferably in the vicinity of 30° C.; the culture pH is set to be in the range of 5 to 8, and preferably 6 to 7. Conditions other than these can be used if the microorganism grows under those other conditions.

The cultivation period can generally be from 1 to 4 days, and within this time, the microorganisms grow, produce and accumulate the pyruvate oxidase in their cells.

The enzyme of this invention can be extracted and purified by the usual methods from bacterial cells. As to methods extracting the enzyme from the cells, the mechanical method of disintegration of the cells can be achieved by the use of ultrasonicator, glass beads, French press, surface-active agents and others. The extract (crude enzyme solution) obtained in this way can be purified by the use of a salting-out technique with ammonium sulfate, sodium sulfate, etc., by the metal aggregation method with the use of magnesium chloride, calcium chloride, etc., by the aggregation method with the use of protamine, polyethyleneimine, etc., by ion-exchange chromatography with the use of DEAE (diethylaminoethyl) sepharose, CM (carboxymethyl) sepharose, etc., and so on.

The activity of the resulting pyruvate oxidase can be measured as follows:

| Reagents for the measurement of activity | |
| --- | --- |
| 0.15 M K-Phosphate buffer (pH 7.0) | 10 ml |
| 0.3% 4-Aminoantipyrine | 1 ml |
| 0.6% Phenol | 1 ml |
| 6 mM Thiamine pyrophosphate | 1 ml |
| 0.3 mM FAD.Na$_2$ | 1 ml |
| 150 U/ml Peroxidase | 1 ml |
| 30 mM EDTA.Na$_2$ | 1 ml |
| 0.3 M MgSO$_4$ | 1 ml |
| Distilled water | 8 ml |

First, from the mixture of the ingredients listed above, 2.5 ml is sampled and placed in a test tube, and 0.5 ml of a 0.3 M solution of potassium pyruvate is added thereto. The mixture is then heated at 37° C. for 5 minutes. To this, 0.05 ml of the enzyme solution is added, and the mixture gently stirred; then, the changes (ΔOD) in the optical density at 500 nm over 1 minute of the mixture at 37° C. are monitored in a spectrophotometer against water. Next, in place of the enzyme solution, 0.05 ml of a 50 mM potassium phosphate buffer (pH 7.0) is used, and the same steps as above are followed to measure the changes (ΔOD) in optical density over 1 minute; this is the blank test. Under these conditions, the enzyme activity of pyruvate oxidase that produces 1 μmol of hydrogen peroxide is taken to be one unit (U).

The physicochemical characteristics of the enzyme activity of this invention will be shown below.

Actions: The enzyme catalyzes the reaction shown below in Equation I, in which it produces acetyl phosphate, carbon dioxide, and hydrogen peroxide from pyruvic acid, inorganic phosphate, and oxygen.

$$CH_3COCOOH + HOPO_3^{2-} + O_2 \rightarrow CH_3COOPO_3^{2-} + CO_2 + H_2O_2 \quad (I)$$

Substrate specificity: The enzyme is specific for pyruvic acid. It does not catalyze oxaloacetic acid, DL-lactic acid, acetic acid, or α-ketoglutaric acid.

Optimum pH: In the vicinity of pH 5.7.

Heat stability: 45° C. or less (at pH 7.0 and for 10 minutes)

Km: For pyruvic acid, about $4 \times 10^{-4}$ M

Molecular weight: About 160,000 (by gel filtration on Sephacryl S-300)

Isoelectric point: About 4.4 (by electrofocusing with carrier ampholytes)

Cofactors: Thiamine pyrophosphate and FAD

The analytical method of this invention makes use of a pyruvate oxidase with excellent thermal stability, such pyruvate oxidase as produced by the microorganism mentioned above, for example. As to the thermal stability, the pyruvate oxidase obtained from the microorganism mentioned above isolated by the inventors is suitable, but it is possible to use any pyruvate oxidase that is stable at pH 7.0 for 10 minutes when heated at temperatures of up to 45° C. When this kind of pyruvate oxidase is used, it is possible to analyze with a high degree of accuracy the compounds involved in the reaction catalyzed by the pyruvate oxidase and also to analyze the enzymes and substrates involved in the said reaction. For example, it is possible to measure or assay the following in all kinds of samples (serum and other body fluids, foods, and other samples, with no special limitation): the amount of pyruvic acid in such samples, the amount of enzyme in the enzyme reaction system that produces pyruvic acid, the amount of substrate in the enzyme reaction system that produces pyruvic acid, etc. For example, it is possible to measure the enzymes and substrates of 1-4 that follow.

1. Glutamic-pyruvic transaminase, α-ketoglutaric acid
2. Glutamic-oxaloacetic transaminase
3. Lactate dehydrogenase, lactic acid
4. Pyruvate kinase, ADP In the method of this invention, for the measurement of pyruvic acid or of the enzymes and substrates related to the enzyme reaction that produces pyruvic acid, a reagent that includes the pyruvate oxidase of this invention are added into a system that contains pyruvic acid. In this reagent, there are FAD, thiamine pyrophosphate, and phosphates in addition to the pyruvate oxidase mentioned above. Moreover, in order that the enzyme reaction should occur smoothly, at least one metal ion selected from the list of magnesium ion, cobalt ion, manganese ion, and calcium ion is preferably added. The amount of pyruvate oxidase and other compounds in the reagent can be any amount provided that the enzyme reaction catalyzed by pyruvate oxidase will proceed satisfactorily. The amount of pyruvate oxidase in the reagent is set depending upon the temperature of the enzyme reaction, the time, etc. In the reagent of this invention, for example, about 0.1-20 U/ml of the pyruvate oxidase with excellent thermal stability, about 5-50 mM inorganic phosphate, about 1-20 μM FAD, about 100-500 μM of thiamine pyrophosphate, and about 1-50 mM metal ion are contained per milliliter of reagent. Moreover, an appropriate buffer is included so that the reaction will occur at the pH of 6-7.5.

When the reagent mentioned above is added, the pyruvic acid in the sample goes through the enzymatic reaction shown in the above Equation I, and acetyl phosphate, carbon dioxide, and hydrogen peroxide are produced. By the measurement of the amounts of hydrogen peroxide, carbon dioxide, and acetyl phosphate produced according to Equation I and/or by the measurement of the amounts of oxygen and inorganic phosphate consumed in the reaction, the amount of pyruvic acid in the sample can be calculated. In particular, the method of measurement of the hydrogen peroxide that is produced can be widely used. The amount of hydrogen peroxide in the reaction system can be measured by (1) the use of peroxidase and a chromogen, or (2) an enzyme electrode, for example. The chromogen can be used with the following combinations:

(1.1) 4-Aminoantipyrine and phenol
(1.2) 4-Aminoantipyrine and N,N-dimethylaniline
(1.3) Methylbenzothiazolinehydrazone (MBTH) and N-ethyl-N-sulfopropyl-m-anisidine (ESPAS), or
(1.4) 4-Aminoantipyrine and N-ethyl-(2-hydroxy-3-sulfopropyl)-m-toluidine (EHSPT)

In the method mentioned above in which peroxidase and a chromogen are used, when, for example, system 1.1 is used, the reaction solution contains peroxidase (about 1-10 U/ml), 4-aminoantipyrine (about 0.005-0.05%), and phenol (about 0.01-0.1%) in the reaction system.

In this way, the amount of pyruvic acid in the reaction system can be measured. The measurement of the compounds related to the production of pyruvic acid and of the enzyme related to the production of pyruvic acid (for example, the measurement of the enzyme activity in the enzyme system that produces pyruvic acid, the measurement of the amount of the enzyme of the enzyme reaction system that produces pyruvic acid, and the measurement of the substrates in the enzyme reaction system that produces pyruvic acid) can be accomplished by the measurement of the above-mentioned pyruvic acid by known methods.

The pyruvate oxidase of this invention can also be used as an immobilized enzyme when fixed to an appropriate carrier. For example, the enzyme can be used fixed to a membrane for enzyme electrodes or to beads.

EXAMPLE 1

First, 90 ml of a culture medium (pH 7.0) that contained meat extract 0.2%, polypeptone 1%, yeast extract 0.4%, Tween 80 0.1% (v/v), $K_2HPO_4.3H_2O$ 0.25%, sodium acetate.$3H_2O$ 0.5%, diammonium citrate 2%, $MgSO_4.7H_2O$ 0.02%, and $MnSO_4.7H_2O$ 0.02% was put into a Sakaguchi flask with a 500-ml capacity, and autoclaved at 121° C. for 15 minutes. The medium was cooled and 10 ml of a 5% aqueous solution of sodium pyruvate that had been filtered so as to remove microorganisms was added to this medium. The medium obtained (medium A) was inoculated with a platinum loop of Lactobacillus sp. TE6103 and cultured for 24 hours at 30° C. This was the seed culture. Next, 5.4 l of fresh medium A was put into a 10-l jar fermentor and autoclaved at 121° C. for 15 minutes. The medium was cooled and 600 ml of a 5% aqueous solution of sodium pyruvate that had been filtered so as to remove microorganisms was added to it. To this mixture, 100 ml of the seed culture was added, followed by agitation at 300 rpm with 2 l of aeration per minute during the 24 hours of cultivation at 30° C. The culture fluid was kept at above pH 6.5 with the use of the needed amount of 10 N NaOH. The activity of the pyruvate oxidase in the resulting culture fluid was 23 mU/ml.

Next, 6 l of this culture broth was centrifuged and the bacterial cells were obtained. These bacterial cells were suspended in 100 ml of a 50 mM potassium phosphate buffer (pH 7.0). The suspension was disrupted with an ultrasonic disintegrator (Kaijo Denki, 19 KHz) for 15 minutes. The resulting mixture was centrifuged to remove debris. The supernatant thus obtained was applied on a column of DEAE-Sepharose CL-6B (Pharmacia) equilibrated with 50 mM potassium-phosphate buffer, and after washing the column with two column volumes of the same buffer, the adsorbed enzyme was eluted with a NaCl density gradient (0–0.5 M). The fractions having pyruvate oxidase activity was combined. The elutes were concentrated with use of an ultrafilter, applied on a column of Sephadex G-25 equilibrated with 50 mM potassium-phosphate buffer (pH 7.0), and desalted. In the desalted solution, the activity of pyruvate oxidase was 60 U. Separately, the same steps as described above were used, except that instead of desalting on a Sephadex G-25 column, gel filtration with Sephandex G-200 (Pharmacia) was carried out. The activity of the pyruvate oxidase obtained was 54 U.

Figure 2:
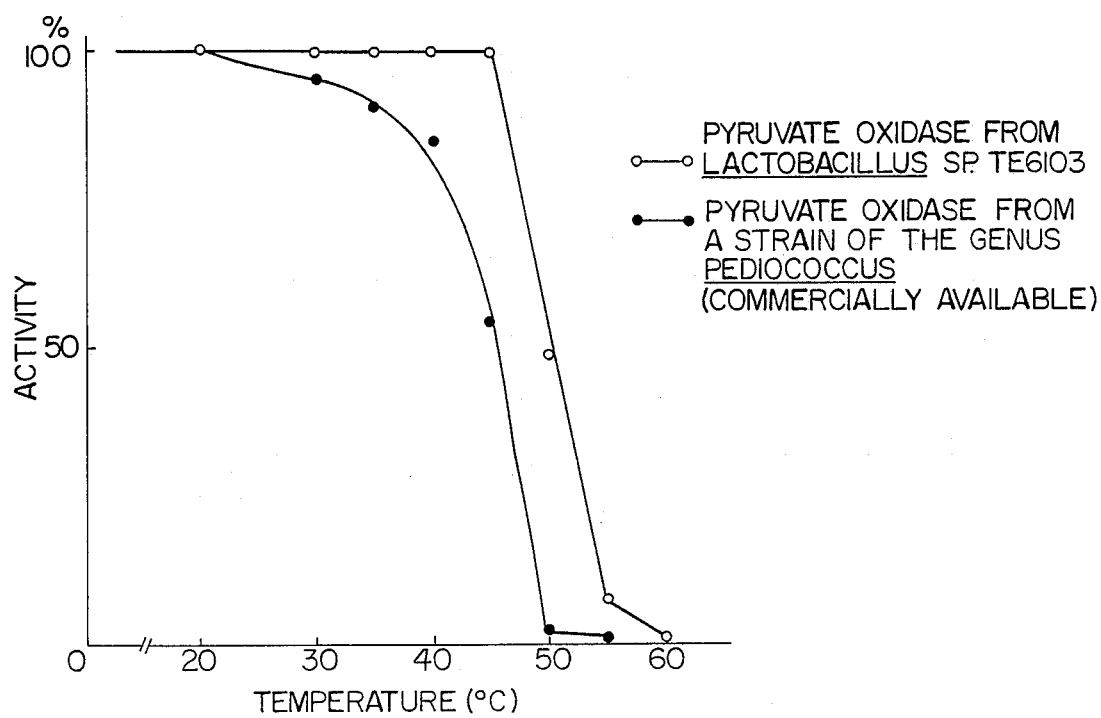
FIG. 2 shows the thermal stability of the pyruvate oxidase of this invention and of the conventional pyruvate oxidase.

The activity of the pyruvate oxidase obtained by desalting as described above was measured in reaction systems, with different pH. The results are shown in FIG. 1. When the pH of the reaction system was 5–6.5, the solvent used was 50 mM acetate buffer, and when the pH of the reaction system was 6–8, the solvent used was 50 mM potassium-phosphate buffer. The activity of pyruvate oxidase, after the pyruvate oxidase was kept for 10 minutes at pH 7.0 at a variety of different temperatures, was measured, and the results are shown in FIG. 2 as open circles.

Comparison 1

The thermal-stability of a commercial preparation of pyruvate oxidase produced by a strain of Pediococcus was measured in the same way as in Example 1. The results are shown in FIG. 2 as closed circles.

EXAMPLE 2

| Formulation of analytical reagent | |
|---|---|
| PIPES buffer (pH 7.0) | 50 mM |
| FAD.Na$_2$ | 10 μM |
| Thiamine pyrophosphate | 0.2 mM |
| MgSO$_4$ | 10 mM |
| KH$_2$PO$_4$ | 5 mM |
| 4-Aminoantipyrine | 0.01% |
| Phenol | 0.02% |
| Peroxidase | 5 U/ml |
| Pyruvate oxidase (that obtained in Example 1) | 2 U/ml |

Figure 3:
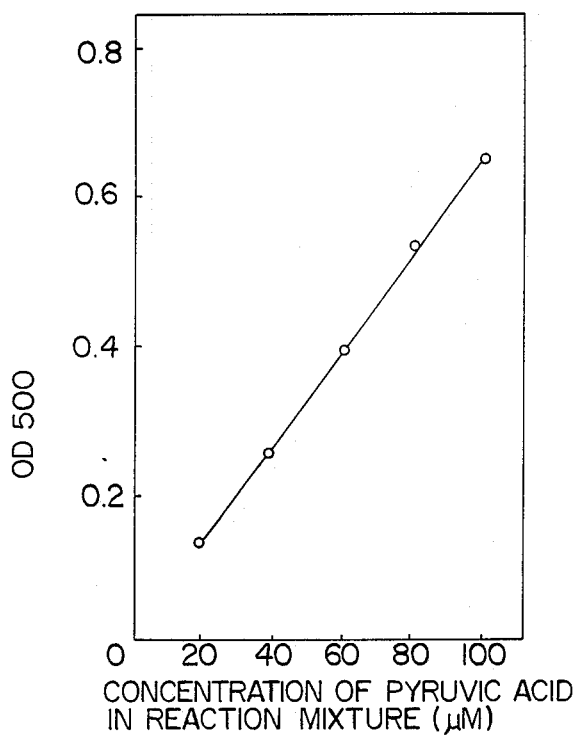
FIG. 3 is a standard curve showing the relationship between the concentration of pyruvic acid in sample solutions and the optical density at 500 nm of the sample solution when the pyruvic acid of the sample solutions is measured by the use of the pyruvate oxidase of this invention.

First, 3 ml of the above-mentioned formulation was heated at 37° C. for about 5 minutes. To this, 20 μl of an aqueous solution of potassium pyruvate (3–15 mM) was added. The mixture was allowed to react for 10 minutes at 37° C. The optical density at 500 nm of the reaction mixture was then measured. The results are shown in FIG. 3. It can be seen from FIG. 3 that the relationship of the concentration of pyruvate in the reaction mixture with the optical density (OD) is proportional.

EXAMPLE 3

| | |
|---|---|
| PIPES buffer (pH 7.0) | 50 mM |
| FAD.Na$_2$ | 10 μM |
| Thiamine pyrophosphate | 0.2 mM |
| MgSO$_4$ | 10 mM |
| KH$_2$PO$_4$ | 5 mM |
| Phosphoenolpyruvic acid | 0.5 mM |
| Pyruvate kinase | 10 U/ml |
| 4-Aminoantipyrine | 0.01% |
| Phenol | 0.02% |
| Peroxidase | 5 U/ml |
| Pyruvate oxidase (that obtained in Example 1) | 2 U/ml |

Figure 4:
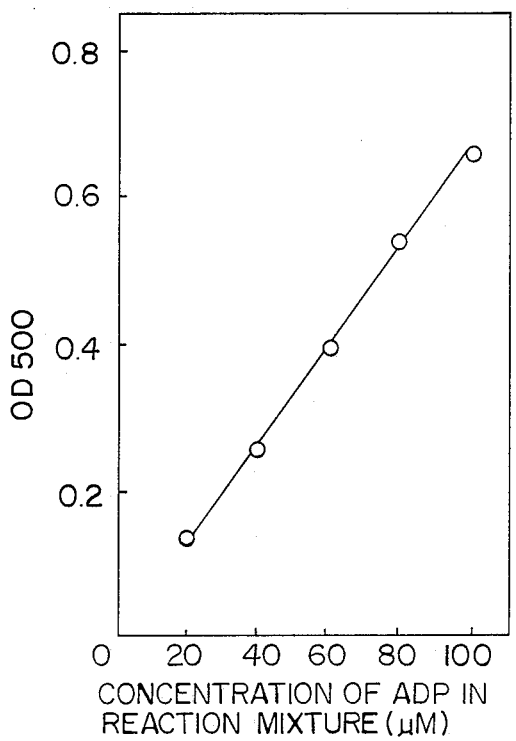
FIG. 4 is a standard curve showing the relationship between the concentration of ADP in sample solutions and the optical density at 500 nm of the sample solution when the ADP of the sample solution is measured by the use of the pyruvate oxidase of this invention.

First, 3 ml of the above-mentioned formulation was heated at 37° C. for about 5 minutes. Then 20 μl of an aqueous solution of ADP (3–15 mM) is added thereto. The mixture was allowed to react at 37° C. for 10 minutes. Then the optical density at 500 nm of the reaction mixture was measured. The results, shown in FIG. 4, indicate that the relationship of the concentration of ADP in the reaction mixture with the optical density (OD) is proportional.

EXAMPLE 4

| Formulation of analytical reagent | |
|---|---|
| PIPES buffer (pH 7.0) | 50 mM |
| FAD.Na$_2$ | 10 μM |
| Thiamine pyrophosphate | 0.2 mM |
| MgSO$_4$ | 10 mM |
| KH$_2$PO$_4$ | 5 mM |
| 4-Aminoantipyrine | 0.01% |
| Phenol | 0.02% |
| Peroxidase | 5 U/ml |
| Pyruvate oxidase (that obtained in Example 1) | 3 U/ml |

Figure 5:
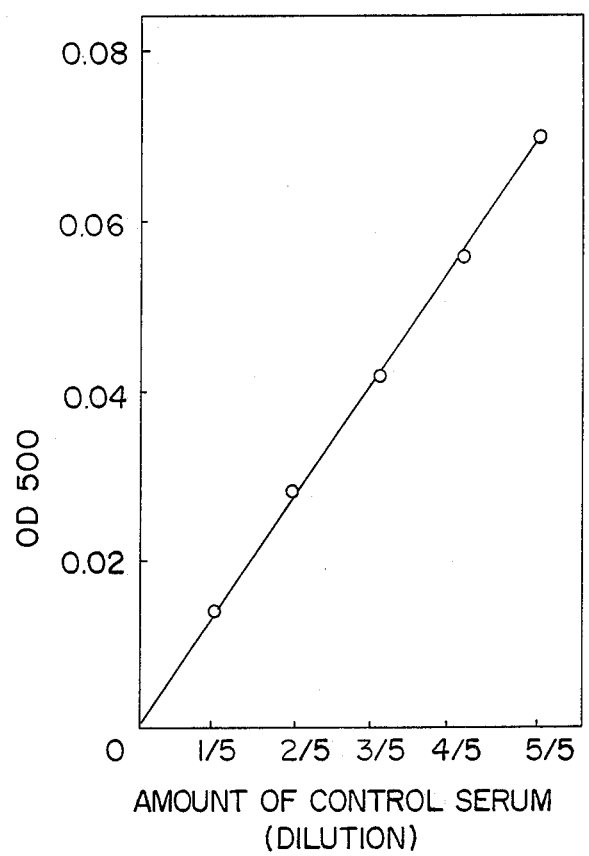
FIG. 5 shows the relationship between the amount of control serum of sample solutions and the optical density at 500 nm of the sample solutions when the pyruvic acid of the control serum is measured by the use of the pyruvate oxidase of this invention.

First, 3.0 ml of the above-mentioned formulation was heated at 37° C. for about 5 minutes. Separately, a given volume of control serum (Q-pak I; 0.2–1.0 ml) was diluted to make 1.0 ml and this was used as a sample. Then 0.2 ml of the sample was added to the above reagent. The mixture was allowed to react at 37° C. for 10 minutes, and its optical density at 500 nm was then measured. The results, shown in FIG. 5, indicate that the relationship of the amount of serum in the reaction mixture and the optical density (OD) is proportional. The standard curve (in FIG. 3) of the results of Example 2 can be used to calculate that the concentration of pyruvic acid in this serum sample was 147 μM.

EXAMPLE 5

Formulation of analytical reagent

| Formulation of analytical reagent | |
| --- | --- |
| PIPES buffer (pH 7.0) | 50 mM |
| FAD.Na$_2$ | 10 μM |
| Thiamine pyrophosphate | 0.2 mM |
| MgSO$_4$ | 10 mM |
| KH$_2$PO$_4$ | 5 mM |
| 4-Aminoantipyrine | 0.01% |
| Phenol | 0.02% |
| Peroxidase | 5 U/ml |
| Pyruvate oxidase (that obtained in Example 1) | 3 U/ml |

Figure 6:
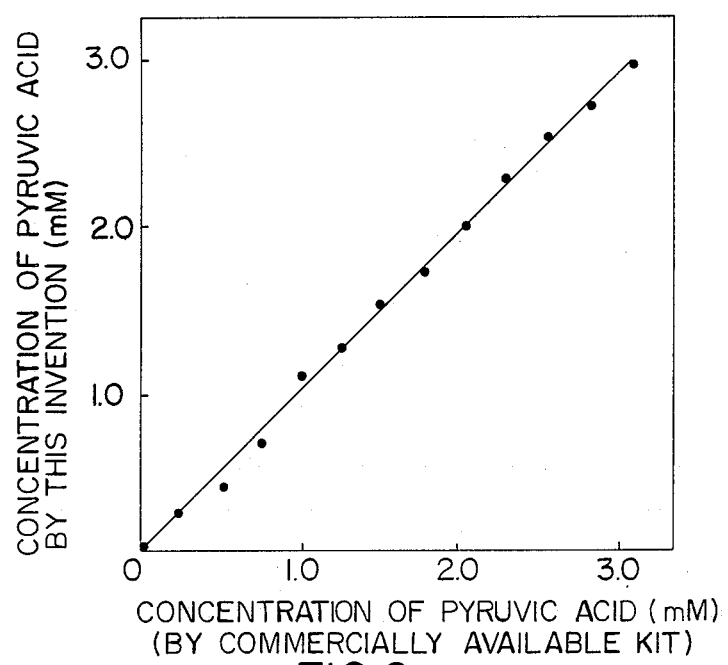
FIG. 6 shows the correlation between the values obtained when the pyruvic acid of sample solutions is measured by the use of a commercially available assay reagent and the values obtained when pyruvic acid of the sample solutions is measured by the use of the reagent of this invention.

First, 3,0 ml of the formulation described above was heated for about 5 minutes at 37° C. To this, 0.1 ml of an aqueous solution of pyruvic acid at a given concentration (0–3 mM) was added, and the mixture was allowed to react for 10 minutes at 37° C. Then the color of the reaction fluid at 500 nm was measured. Next, in the same way as above, the aqueous solution of pyruvic acid was measured by the use of a commercially available kit for the assay of pyruvic acid (Determiner-PA, Kyowa Medics). The results when a sample (an aqueous solution of pyruvic acid) was used and measurements were made according to this invention were plotted on the y-axis, and the results when the same sample was measured with use of the commercially available kit were plotted on the x-axis. The graph obtained is shown in FIG. 6. The correlation of the values measured by the use of this invention with the values measured in the conventional way was r=0.979 (n=30), and the correlation equation was y=0.95x+0.03, which indicates very good correlation.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed is:

1. A pyruvate oxidase with excellent thermal stability, which has the following characteristics:
   (1) it retains substantially 100% activity at pH 7.0 for 10 minutes at a temperature of up to 45° C.; and
   (2) its optimum pH is pH 5.7.
2. A pyruvate oxidase according to claim 1, which has the following characteristics:
   (1) it catalyses a reaction that produces acetyl phosphate, carbon dioxide, and hydrogen peroxide from pyruvic acid, inorganic phosphate, and oxygen;
   (2) it acts specifically on pyruvic acid; and
   (3) it requires thiamine pyrophosphate and FAD as cofactors.
3. A pyruvate oxidase according to claim 1, which has the following characteristics:
   (1) it catalyses a reaction that produces acetyl phosphate, carbon dioxide, and hydrogen peroxide from pyruvic acid, inorganic phosphate, and oxygen;
   (2) it acts specifically on pyruvic acid;
   (3) it requires thiamine pyrophosphate and FAD as cofactors;
   (4) its molecular weight is about 160,000 (measured by gel filtration on Sephacryl S-300);
   (5) the $K_m$ for pyruvic acid is about $4 \times 10^{-4}$ M; and
   (6) its isoelectric point is about 4.4 (measured by electrofocusing with carrier ampholytes).
4. A pyruvate oxidase according to claim 1, which is produced by the strain of Lactobacillus sp. TE-6103 (FERM BP-1419).
5. An analytical method comprising:
   adding a reagent to a sample containing pyruvic acid, wherein said reagent comprises the pyruvate oxidase of claim 1, FAD, thiamine pyrophosphate, and phosphates; and
   measuring the amount of acetyl phosphate, carbon dioxide, hydrogen peroxide, oxygen, or inorganic phosphate produced or consumed.
6. An analytical method according to claim 5, wherein said pyruvate oxidase has the following characteristics:
   (1) it catalyses a reaction that produces acetyl phosphate, carbon dioxide, and hydrogen peroxide form pyruvic acid, inorganic phosphate, and oxygen;
   (2) it acts specifically on pyruvic acid; and
   (3) it requires thiamine pyrophosphate and FAD as cofactors.
7. An analytical method according to claim 5, wherein said pyruvate oxidase has the following characteristics:
   (1) it catalyses a reaction that produces acetyl phosphate, carbon dioxide, and hydrogen peroxide from pyruvic acid, inorganic phosphate, and oxygen;
   (2) it acts specifically on pyruvic acid;
   (3) it requires thiamine pyrophosphate and FAD as cofactors;
   (4) its molecular weight is about 160,000 (measured by gel filtration on Sephacryl S-300);
   (5) the $K_m$ for pyruvic acid is about $4 \times 10^{-4}$ M; and
   (6) its isoelectric point is about 4.4 (measured by electrofocusing with carrier ampholytes).
8. An analytical method according to claim 5, wherein said pyruvic oxidase is produced by the strain of Lactobacillus sp. TE-6103 (FERM BP-1419).
9. An analytical reagent containing the pyruvate oxidase in claim 1, FAD, thiamine pyrophosphate, inorganic phosphate, and at least one metal ion selected from the group consisting of magnesium ion, cobalt ion, manganese ion, and calcium ion.
10. An analytical reagent according to claim 9, wherein said pyruvate oxidase has the following characteristics:
    (1) it catalyses a reaction that produces acetyl phosphate, carbon dioxide, and hydrogen peroxide from pyruvic acid, inorganic phosphate, and oxygen;

(2) it acts specifically on pyruvic acid; and (3) it requires thiamine pyrophosphate and FAD as cofactors.

11. An analytical reagent according to claim 9, wherein said pyruvate oxidase has the following characteristics:

(1) it catalyses a reaction that produces acetyl phosphate, carbon dioxide, and hydrogen peroxide from pyruvic acid, inorganic phosphate, and oxygen;

(2) it acts specifically on pyruvic acid;

(3) it requires thiamine pyrophosphate and FAD as cofactors;

(4) its molecular weight is about 160,000 (measured by gel filtration on Sephacryl S-300);

(5) the $K_m$ for pyruvic acid is about $4 \times 10^{-4}$ M; and (6) its isoelectric point is about 4.4 (measured by electrofocusing with carrier ampholytes).

12. An analytical reagent according to claim 9, wherein said pyruvate oxidase is produced by the strain of Lactobacillus sp. TE-6103 (FERM BP-1419).

* * * * *